United States Patent [19]

Lolachi

[11] 4,056,224
[45] Nov. 1, 1977

[54] FLOW SYSTEM FOR CENTRIFUGAL LIQUID PROCESSING APPARATUS

[75] Inventor: Houshang Lolachi, Rockville, Md.

[73] Assignee: Baxter Travenol Laboratories, Inc., Deerfield, Ill.

[21] Appl. No.: 657,186

[22] Filed: Feb. 11, 1976

Related U.S. Application Data

[63] Continuation-in-part of Ser. No. 562,749, March 27, 1975, abandoned.

[51] Int. Cl.² .......................... B04B 5/02; B04B 7/00; B04B 15/12
[52] U.S. Cl. .................................... 233/14 R; 233/26
[58] Field of Search .................. 233/25, 26, 27, 14 R, 233/14 A, 1 R, 23 R, 19 R, 15, 23; 210/DIG. 24, 31 C, 198 C; 285/332

[56] References Cited

U.S. PATENT DOCUMENTS

| | | | |
|---|---|---|---|
| 3,514,131 | 5/1970 | McKinney | 285/332 |
| 3,655,123 | 4/1972 | Judson | 233/14 R |
| 3,672,564 | 6/1972 | Schlutz | 233/26 |
| 3,885,735 | 5/1975 | Westbert | 233/25 |

Primary Examiner—George H. Krizmanich
Attorney, Agent, or Firm—Henry W. Collins; Richard G. Kinney; Eugene M. Cummings

[57] ABSTRACT

A seal-less disposable flow system for use in conjunction with a centrifugal liquid processing apparatus or the like wherein a rotor assembly for subjecting a liquid to be processed to centrifugation is rotatably mounted on a rotor drive assembly, which is rotatably mounted to a stationary base. The rotor assembly is rotatably driven in the same direction as the rotor drive assembly with a speed ratio of 2:1. The flow system includes two containers adapted for mounting on the rotor assembly and a flexible umbilical cable which extends from the containers to a location external to the apparatus by way of a passageway provided in the support shaft of the rotor assembly and guide means carried on and rotatably mounted to the rotor drive assembly to maintain liquid communication with the containers during rotation of the rotor without the use of rotating seals. A reusable leader assembly facilitates installation of the flow system in the processing apparatus.

9 Claims, 8 Drawing Figures

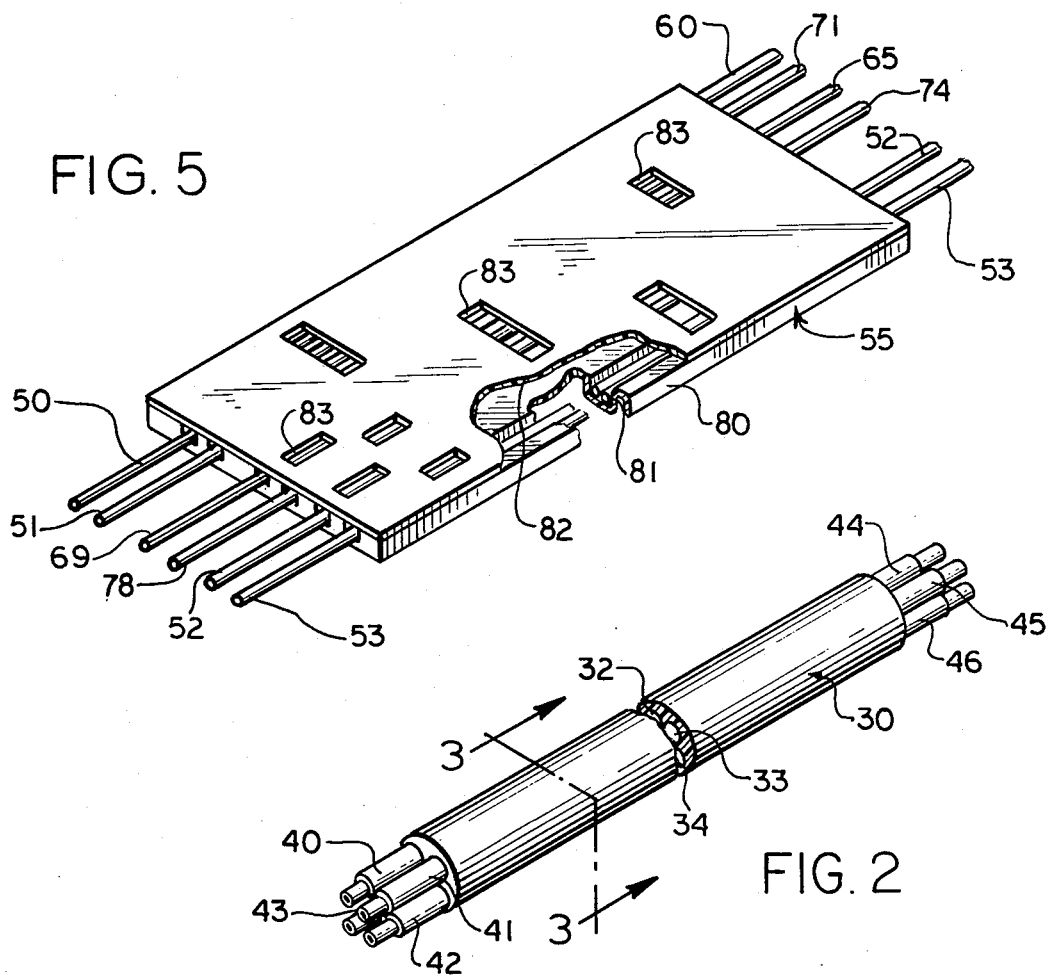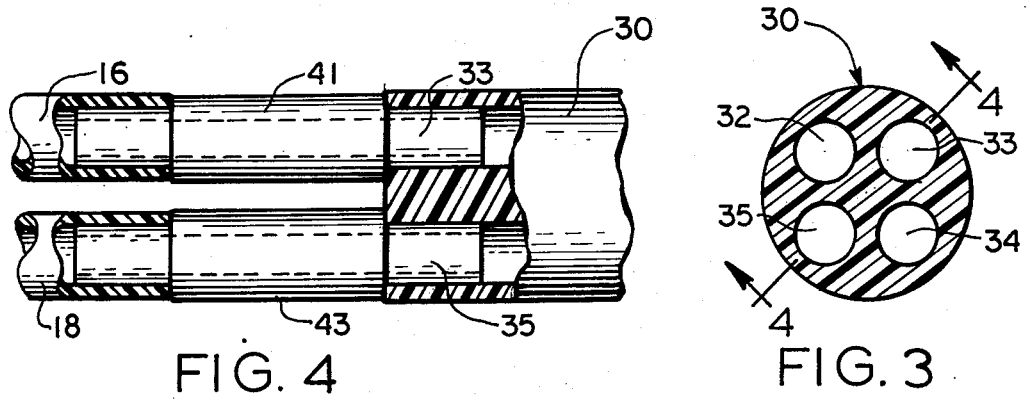

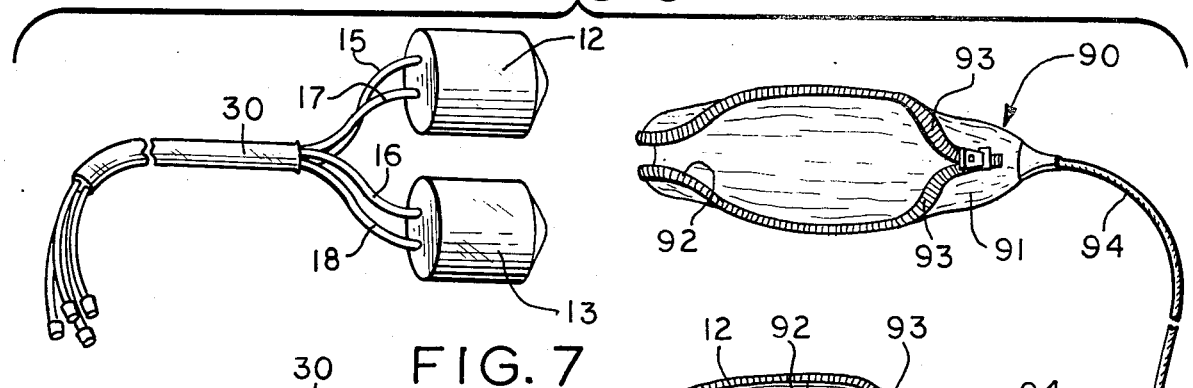
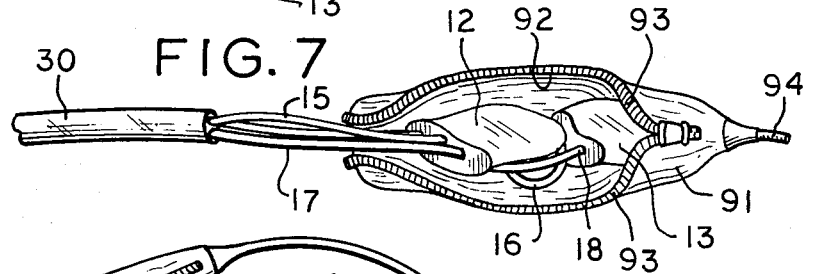
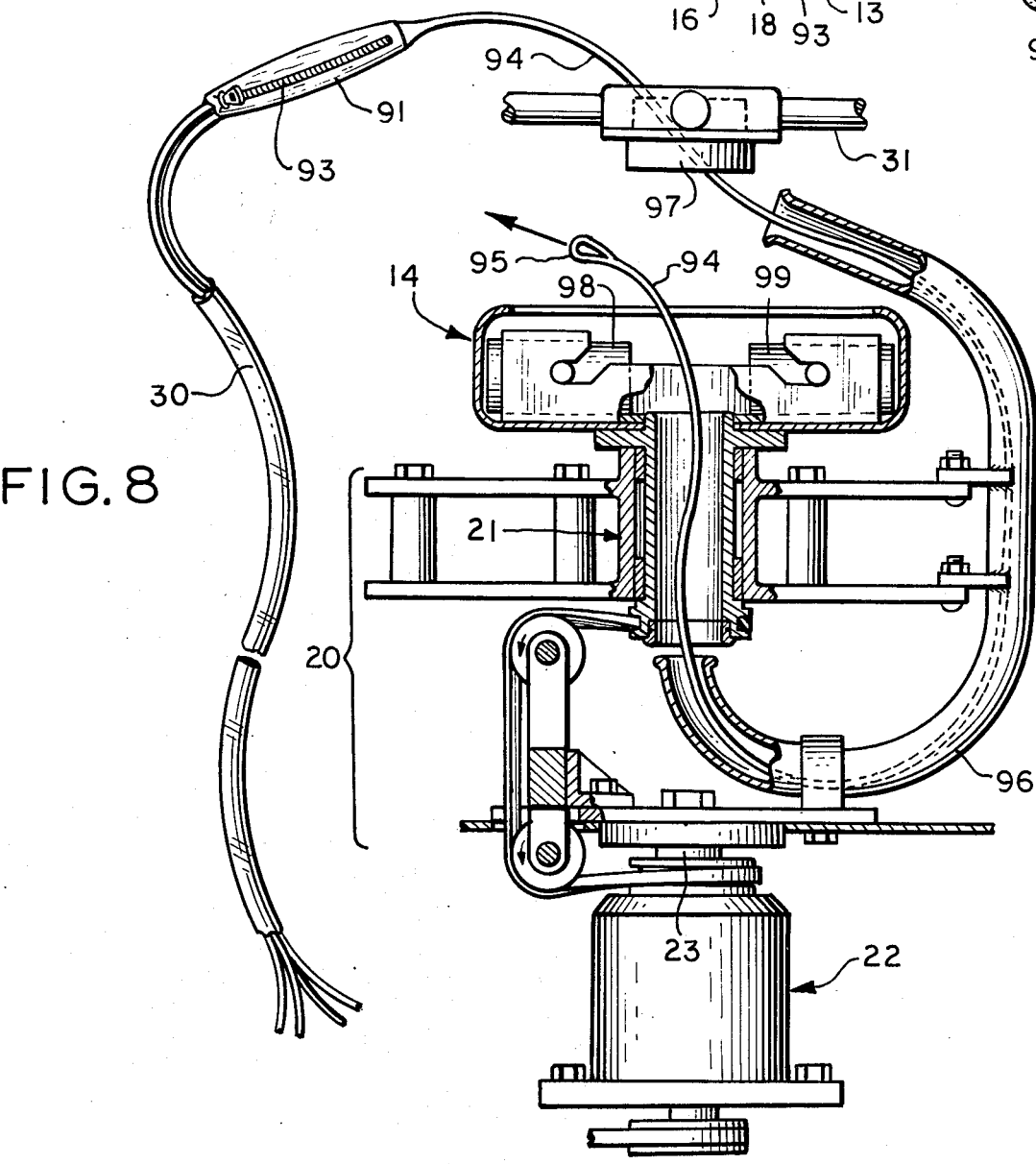

FLOW SYSTEM FOR CENTRIFUGAL LIQUID PROCESSING APPARATUS

This application is a continuation-in-part of application Ser. No. 562,749, filed Mar. 27, 1975, and now abandoned.

BACKGROUND OF THE INVENTION

The present invention is directed generally to a fluid flow system, and more particularly to a pre-sterilized disposable flow system for processing blood and other biological cells while under centrifugation which does not utilize a rotating seal member.

In recent years long term storage of human blood has been accomplished by separating out the plasma component of the blood and freezing the remaining red blood cell component in a liquid medium such as glycerol. Prior to use, the glycerolized red blood cells are thawed and pumped into a centrifugating wash chamber where, while being held in place by centrifugation, they are washed with a saline solution which displaced the glycerol preservative. The resulting reconstituted blood is then removed from the wash chamber and packaged for use.

The aforedescribed blood conditioning process necessitates the transfer of glycerolized cell and saline wash solutions into the wash chamber, and the transfer of glycerol waste and reconstituted blood from the wash chamber, while the chamber is in motion.. To avoid contamination of the blood or the exposure of persons involved in the processing operation to infection these fluid transfer operations must be carried out within a sealed pre-sterilized flow system, preferably formed of a flexible plastic or similar material which can be disposed of after each use.

One drawback present in many such flow systems has been their use of a rotating seal or coupling element between that portion of the system carried by the centrifuge rotor and that portion of the system which remains stationary. While such rotating seals have provided generally satisfactory performance, they have been expensive to manufacture and have unnecessarily added to the cost of the flow systems. Furthermore, such rotating seals do introduce an additional component into the system which if defective can cause contamination of the blood being processed. This is particularly true when two different batches of blood are being simultaneously processed since the components of one blood batch must pass side-by-side through the rotating seal with the components of another blood batch.

One flow system heretofore contemplated to overcome the problem of the rotating seal utilizes a rotating carriage on which a single housing is rotatably mounted. An umbilical cable extending to the housing from a stationary point imparts planetary motion to the housing and thus prevents the cable from twisting. To enable fluid to be centrifugally processed an inner wash chamber is rotatably mounted within the housing and connected to the umbilical cable by a rotating seal. A weight on the chamber causes the chamber to be radially aligned as the rotor turns to maintain a constant centrifugal force field on the fluid. Unfortunately, this arrangement requires the use of an expensive and trouble-prone rotating seal, albeit in the housing, and allows the use of only one wash chamber, preventing the simultaneous processing of multiple batches of cells.

Thus the need exists for a centrifugal cell processing system wherein multiple batches of cells can be simultaneously and efficiently processed without the use of rotational coupling elements. In the co-pending application of the present applicant, Ser. No. 657,187, filed Feb. 11, 1976, a continuation-in-part of application Ser. No. 562,748, filed Mar. 27, 1975 and assigned to the present assignee, a centrifugal cell processing system and apparatus are described which encompass the principle of operation of apparatus described in U.S. Pat. No. 3,586,413 to Dale A. Adams, and which avoid the use of rotary coupling elements. The present invention is directed to a disposable flow system for use in that system.

SUMMARY OF THE INVENTION

The invention is directed to a disposable flow system for use in conjunction with the centrifugal cell processing apparatus of the type having a stationary base, a rotor drive assembly rotatably mounted to the base for rotation along a predetermined axis, a rotor assembly including means for receiving at least one cell processing chamber, the rotor assembly being rotatably mounted with respect to the base for rotation along the axis, guide means for causing rotation of an operatively engaged cable segment with the rotor drive assembly about the axis, and drive means for rotating the rotor assembly and the rotor drive assembly in the same direction with a speed ratio of 2:1. The flow system comprises at least one cell processing chamber adapted to be mounted on the rotor, a container for containing cells to be washed, a container for containing wash solution, and means including a flexible umbilical cable segment having at least one passageway in communication with the processing chamber for selectively establishing flow communication with the cell and wash containers.

The invention is further directed to a leader assembly for installing a flow system of the type having at least one flexible-walled liquid processing chamber and a connecting flexible conduit segment in a centrifugal processing apparatus having guide means through which the processing chamber and conduit segment are threaded. The leader assembly comprises a pouch including an opening through which the processing chamber is stuffed into the pouch and a flexible guide cable attached to one end of the pouch for pulling the pouch through the guide means.

BRIEF DESCRIPTION OF THE DRAWINGS

The features of the present invention, which are believed to be novel, are set forth with particularity in the appended claims. The invention, together with the further objects and advantages thereof, may best be understood by reference to the following description taken in connection with the accompanying drawings, in the several figures of which like reference numerals identify like elements, and in which:

FIG. 2 is an enlarged perspective view of a section of the umbilical cable utilized in the flow system.

FIG. 3 is a cross-sectional view taken along line 3—3 of FIG. 2 showing a construction of the umbilical cable.

FIG. 4 is a cross-sectional view taken along line 4—4 of FIG. 3 showing the coupling arrangement employed between the ends of the umbilical cable and other tubes in the system.

FIG. 5 is an enlarged perspective view of the connector block utilized in the flow system partially broken away to show the construction of the block.

FIG. 6 is a perspective view partially in cross-section of a leader assembly constructed in accordance with the invention conditioned for receiving the wash bags of the flow system.

FIG. 7 is a perspective view partially in cross-section of the pouch portion of the leader assembly showing the wash bags of the flow system contained therein.

FIG. 8 is a front elevational view partially in cross-section showing the leader being utilized to install the flow system in a centrifugal cell processing apparatus.

DESCRIPTION OF THE PREFERRED EMBODIMENT

Figure 1:
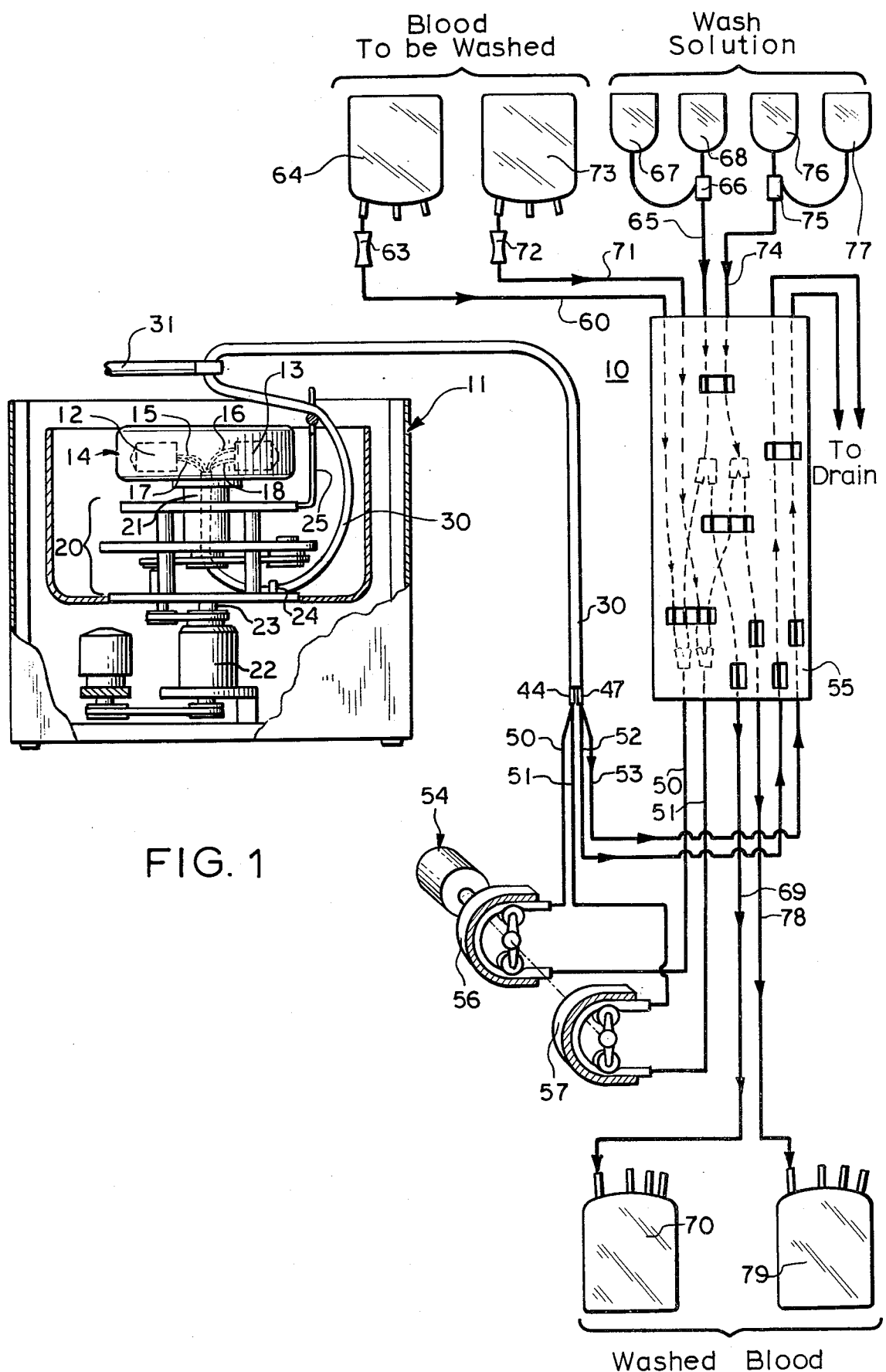
FIG. 1 is a flow diagram partially in pictorial form and partially in schematic form showing a disposable flow system constructed in accordance with the invention for reconstituting red blood cells.

Referring to the Figures, and particularly to FIG. 1, a disposable flow system 10 constructed in accordance with the invention is shown in conjunction with a centrifugal cell processing apparatus 11 constructed in accordance with the aforementioned co-pending continuation-in-part application Ser. No. 562,749, and now abandoned. The flow system includes a pair of cell wash chambers in the form of collapsible plastic bags 12 and 13 in which the cell washing process is carried out under centrifugation. These wash bags, which may be formed of a suitable hemorepellent plastic material such as polyvinylchloride resin, and internally coated with a silicon rubber compound or other hemocompatible material, are preferably formed with a cylindrical body portion and a conical end portion. Cups having complementarily formed cavities (not shown) are provided in the rotor assembly 14 of the cell processing apparatus for receiving the wash bags.

Wash bags 12 and 13 have respective ones of inlet tubes 15 and 16 and outlet tubes 17 and 18 heat-sealed into communication with their interiors. The portions of the inlet tubes 15 and 16 which extend within the interiors of the bags are of sufficient length to extend to the apexes of the cone-shaped end portions of the bags when the bags are fully distended by centrifugal force. This is desirable for optimum washing action, since the cell mass congregates in the conical portions of the wash bags when under centrifugation. Outlet tubes 17 and 18 terminate in the walls of the wash bags. The overall length of the inlet and outlet tubes outside of the containers is not critical and need be only sufficient to provide for connection to the balance of the cell processing system.

The centrifugal cell processing apparatus in which wash bags 12 and 13 are mounted includes a rotor drive assembly 20 to which the rotor assembly 14 is journaled by means of a hollow support shaft 21. The rotor drive assembly 20 is journaled to a stationary hub assembly 22 by means of a vertical drive shaft 23, and includes first and second radially aligned guide members 24 and 25.

Fluid communication is established with wash bags 12 and 13, which rotate with rotor assembly 14, and the non-rotating portion of the flow system by means of a four-channel umbilical cable 30 which extends from a central location between the wash bags axially downwardly through the center of drive shaft 21, radially outwardly through guide member 24, and upwardly through guide member 25 to a fixed axially-aligned position established by support arm 31. As fully described in the previously identified co-pending application of the present applicant, this routing of the umbilical cable 30, together with the rotor assembly 14 and rotor drive assembly 20 being driven in the same direction with a speed ratio of 2:1, establishes fluid communication with wash bags 12 and 13 without the cable becoming twisted. Instead, the umbilical cable is subjected only to flexing, or repeated partial twists about its axis through angles not in excess of 180°, as the rotor assembly 14 rotates.

Referring to FIGS. 2 and 3, the umbilical cable 30 incorporated in flow system 10 includes four symmetrically arranged cylindrical passageways or channels 32–35 for carrying liquids into and out of wash bags 12 and 13. The cable may be formed as a unitary cylindrical extrusion in which the four passageways are extruded, or may be found from individual cables. In a representative extruded umbilical cable wherein four passageways are provided, the cable has an outside diameter of 0.50 inch, and the four passageways 32–35 have a diameter of 0.12 inch and a center-to-center spacing of 0.20 inch. The cable is preferably formed from a polyvinylchloride resin or similar flexible hemocompatible compound, such as polypropylene, polyethylene, teflon, nylon, or silicon, and may include a silicon rubber compound internal lining. The umbilical cable is preferably transparent but may be color-coded by the addition of suitable pigments. The cable is of sufficient length to extend from the center or rotor assembly 14 to a position 36 wherein it can connect with discrete tubing segments, and in a typical application may be approximately 60 inches in length.

Referring to FIGS. 2 and 4, the four passageways 32–35 contained in umbilical cable 30 may be coupled to respective ones of the inlet tubes 15 and 16 and outlet tubes 17 and 18 associated with wash bags 12 and 13 by appropriate means such as luer-type fittings 40–43, respectively. The luer fittings each include projecting male portions of reduced diameter which are received within the passageways of umbilical cable 30 and the inlet and outlet tubes from the wash bags. This establishes a compact streamlined connection suitable for use in the restricted confines of rotor assembly 14. Furthermore, the excellent mechanical integrity provided by this connection enables all of the movable components of flow system 10, i.e., wash bags 12 and 13, tubes 15-18, luer fittings 40-43 and the portion of umbilical cable 30 extending to arm 31, to be passed through guide members 24 and 25 and the center passageway through drive shaft 21 when installing the flow system in the cell processing apparatus.

At the other end of umbilical cable 30 passageways 32–35 may be similarly connected by means of luer fittings 44–47 to respective ones of four tubes 50–53 (FIG. 1). As with the connections established between the inlet and outlet tubes extending from wash bags 12 and 13, the luer fittings in this application establish a mechanically-integral connection.

Tubes 50 and 51, which may be formed of silicon-lined polyvinylchloride or similar material, are routed through a conventional two-section reversible roller pump 54 to a junction block 55 wherein communication is established between these tubes and supplies of glycerolized red blood cells or saline wash solutions, or reservoirs for containing reconstituted blood. Roller pump 54, which may be entirely conventional in design and construction, includes a pair of arcuate mandrels 56 and 57 in which tubes 50 and 51 are seated, and a pair of rotating pressure roller assemblies 58 and 59 which bear against these tubes as they rotate so as to force liquids to flow through the tubes in a direction dependent on the direction of rotation of the roller assemblies.

Tube 50, which connects with passageway 32 in cable 30 and inlet tube 15 of wash bag 12, is connected by Y connectors within junction block 55 to a tube 60, which extends through a filter chamber 63 to a container 64 containing a first batch of glycerolized red blood cells to be processed, and to a tube 65, which extends through a tube clamp valve 66 to a pair of parallel-connected containers 67 and 68 containing saline wash solution for processing the first blood batch. Tube 50 is also connected in block 55 to a tube 69, which connects to a reservoir 70 for receiving blood reconstituted from the first batch of glycerolized red blood cells. Similarly, tube 51 is connected by a tube 71 and a filter 72 to a container 73 containing a second batch of glycerolized red blood cells to be processed, by a tube 74 and a tube clamp value 75 to a pair of parallel-connected containers 76 and 77 containing wash solution for the second blood batch, and by a tube 78 to a container 79 in which blood reconstituted from the second batch of glycerolized red blood cells is received. Tubes 52 and 53, which communicate with passageways 34 and 35 in umbilical cable 30 and with outlet tubes 17 and 18 of wash bags 12 and 13, respectively, pass through block 55 and empty into a drain.

In operation, the two batches of glycerolized red blood cells to be processed are pumped from containers 64 and 73 by roller pump 54 into wash bags 12 and 13 through tubes 50 and 51, umbilical passageways 31 and 32, and inlet tubes 15 and 16, respectively. By reason of the centrifugal force exerted by rotor assembly 14, which may rotate at speeds in excess of 2000 RPM, the red blood cells congregate at the apex of the conical portion of the extended wash bags. Saline wash solution is now pumped from container paris 67, 68 and 76, 77 by roller pump 54 through the same flow path. The saline wash solution flows through the centrifugally-congregated red cell mass, the spent solution flowing out through outlet tubes 17 and 18, umbilical passageways 34 and 35, and tubes 52 and 53 as waste.

This continues until the entire supply of wash solution has been used, the glycerol preservative in the red blood cells being replaced by the saline solution to form reconstituted blood. The reconstituted blood is now pumped from wash bags 12 and 13 through inlet tubes 15 and 16, umbilical passageways 32 and 33, tubes 50 and 51, and tubes 69 and 78, to containers 70 and 79, respectively. Pump 54 is operated in reverse during this operation.

Referring to FIG. 5, junction block 55 includes an injection-molded plastic base 80 in which the various tubes and Y connectors are seated in suitably dimensioned recesses 81. A protective cover 82 is fastened by an appropriate adhesive over the surface of base 80 to hold the tubes and Y connectors in position. The cover is preferably provided with a plurality of apertures or access windows 83 for the purpose of enabling the technician controlling the blood washing process to visually ascertain the flow of the various fluids in the various tubes, and also to enable the application of suitable tube clamps at appropriate locations in the block assembly.

The aforementioned observing and clamping operations can also be performed automatically. For example, a suitable arrangement of photocells could be provided for detecting the flow of the various fluids involved in the cell washing process through the various tubes, either at the access windows 83 of block 55, or at other appropriate locations along the tubes. Suitable solenoid-operated clamping means, controlled by appropriate detection and logic circuitry, could be provided to selectively interrupt the flow of these fluids, either at windows 83 or at appropriate locations along the tube segments.

While the illustrated flow system has two cell processing compartments or wash bags and an umbilical cable having four passageways for simultaneously processing two batches of cells, it will be appreciated that a greater or lesser number of cell processing compartments or wash bags and passageways could be provided to permit simultaneous processing of a lesser or larger number of batches, the only limitation being the amount of available space on the rotor assembly and the practicality of forming the umbilical cable with the required number of passageways.

To facilitate installation of wash bags 12 and 13 of the flow system in the centrifugal cell processing apparatus a leader assembly 90 may be provided, as shown in FIG. 5. This assembly, in accordance with another aspect of the invention, includes retaining means in the form of a flexible-walled pouch 91 formed of heavy plastic or other suitable material having an opening 92 along one side through which access may be gained to the interior of the pouch. The opening is preferably provided with closure means in the form of zipper 93 or the like whereby the contents of the pouch can be secured within. The walls of the pouch are tapered at each end to give the pouch a football-like shape which, as will be seen presently, facilitates installation in the cell processing apparatus.

To enable the pouch to be pulled into the apparatus the front end of the pouch is attached to a semi-flexible cable segment 94 formed of nylon or other suitable material. This cable segment has sufficient rigidity to enable it to be easily threaded through a conduit without becoming tangled, yet is sufficiently flexible to freely negotiate bends in the conduit. The cable segment preferably includes gripping means in the form of a loop or handle portion 95 at its free end for the user to grasp in pulling the leader assembly through the apparatus.

In use, the wash bags 12 and 13 and a portion of their inlet tubes 15 and 16 and outlet tubes 17 and 18 are compressed and stuffed into the interior of the pouch 91, as shown in FIG. 6. To provide the narrowest possible cross section for the pouch the wash bags are preferably aligned one behind the other. The opening 92 of the pouch is then closed by running the zipper along its track as shown in FIG. 7 to secure the wash bags within the pouch.

The flexible cable segment 94 is now threaded into the guide means of the centrifugal processing apparatus, which in FIG. 7 consists of a curved guide sleeve 96 mounted to the rotor drive assembly 20 and extending from a stationary central umbilical cable support hub 97 above the rotor assembly 14 to the bottom end of the rotor drive shaft 21. The construction and operation of this support sleeve, as well as that of the rotor and rotor drive assemblies of the apparatus, are described and claimed in the afore-identified co-pending continuation-in-part application of the present applicant, Serial No.

Once threaded through the guide sleeve the grip end 95 of the cable segment 94 is pushed up through the center of rotor drive shaft 21 until it can be grasped by the user. The grip end is then pulled upwardly until the entire cable portion 94 and pouch 91 are clear of the rotor. The pouch is now opened and the wash bags are pulled out of the pouch and installed in respective ones of containers 98 and 99 provided on the rotor assembly. Excess conduit at the rotor may be taken up by pulling back on the umbilical cable segment 30.

It will be appreciated that while leader 90 is most useful in threading the flow system into a closed guide sleeve, it also is useful in installing the system into processing apparatus not having such a guide sleeve, such as that shown in FIG. 1. Also, in the case of a flow-system where the wash bags are non-collapsible, as when formed of a rigid plastic or similar material, the non-rotating portion of the system, i.e. junction block 55 and containers 64, 67, 68, 70, 73, 76, 77 and 79, together with the interconnecting tubing, may be threaded into the apparatus in the opposite direction, being pushed down through the center of rotor drive shaft and pulled up through the guide sleeve.

The pouch 91 and cable 94 of leader 90 in the illustrated embodiment may have various lengths and thicknesses depending on the size and number of wash bags contained in the flow system and the cross-sectional size of the guide sleeve. Furthermore, the pouch and cable segment may be constructed of other materials such as leather and stainless steel cable, respectively.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A leader assembly for installing a flow system of the type having at least one flexible-walled liquid processing chamber and a connecting flexible conduit segment in a centrifugal processing apparatus having guide means through which the processing chamber and conduit segment are threaded, comprising, in combination:
   retaining means including an opening for receiving the processing chamber; and
   a flexible guide cable attached to said retaining means for pulling said retaining means through the guide means.

2. A leader assembly as defined in claim 1 wherein said retaining means comprise a flexible-walled pouch.

3. A leader assembly as defined in claim 2 wherein said pouch has generally a football-like shape and said guide cable is attached to one end thereof.

4. A leader assembly as defined in claim 1 wherein said guide cable includes a handle portion on the free end thereof.

5. A leader assembly as defined in claim 1 wherein said retaining means and said guide cable are formed of a flexible plastic material.

6. A disposable flow system for use in conjunction with a centrifugal cell processing apparatus of the type having
   a stationary base,
   a rotor drive assembly rotably mounted to the base for rotation along a predetermined axis,
   a rotor assembly including means for receiving at least one cell processing chamber, the rotor assembly being rotatably mounted with respect to said base for rotation along the axis
   guide means for causing rotation of an operatively engaged cable segment with the rotor drive assembly about the axis, and
   drive means for rotating the rotor assembly and the rotor drive assembly in the same direction with a speed ratio of 2:1,
   said flow system comprising, in combination:
   at least one cell processing chamber mounted on the rotor;
   a container for containing cells to be washed;
   a container for containing wash solution;
   means including a flexible umbilical cable segment having at least one passageway in communication with said processing chamber for selectively establishing flow communication with said cell and wash containers; and
   a leader assembly having a pouch portion containing said cell processing chamber, and a flexible cable portion extending from said pouch portion through said guide means for guiding said cell processing chamber through said guide means into position on said apparatus.

7. A flow system as defined in claim 6 wherein said pouch has generally a football-like shape and said guide cable is attached to one end thereof.

8. A flow system as defined in claim 6 wherein said guide cable includes a handle portion on the free end thereof.

9. A flow system as defined in claim 6 wherein said retaining means and said guide cable are formed of a flexible plastic material.

* * * * *